US009980656B2

(12) United States Patent
Chakravarthy et al.

(10) Patent No.: US 9,980,656 B2
(45) Date of Patent: May 29, 2018

(54) HYBRID MODEL AND DIAGNOSTIC PROCESS FOR ATRIAL FIBRILLATION

(71) Applicants: Latha Chakravarthy, Beavercreek, OH (US); Karthik Balaji Chakravarthy, Beavercreek, OH (US); Rohit Vallabh Chakravarthy, Beavercreek, OH (US)

(72) Inventors: Latha Chakravarthy, Beavercreek, OH (US); Karthik Balaji Chakravarthy, Beavercreek, OH (US); Rohit Vallabh Chakravarthy, Beavercreek, OH (US)

(*) Notice: Subject to any disclaimer, the term of this patent is extended or adjusted under 35 U.S.C. 154(b) by 336 days.

(21) Appl. No.: 14/693,532

(22) Filed: Apr. 22, 2015

(65) Prior Publication Data

US 2015/0297096 A1 Oct. 22, 2015

Related U.S. Application Data

(60) Provisional application No. 61/982,719, filed on Apr. 22, 2014.

(51) Int. Cl.
| | |
|---|---|
| *A61B 5/02* | (2006.01) |
| *A61B 5/022* | (2006.01) |
| *A61B 5/046* | (2006.01) |
| *A61B 5/00* | (2006.01) |
| *A61B 8/00* | (2006.01) |
| *A61B 5/0452* | (2006.01) |

(52) U.S. Cl.
CPC .............. *A61B 5/022* (2013.01); *A61B 5/046* (2013.01); *A61B 5/7275* (2013.01); *A61B 5/04525* (2013.01); *A61B 5/6826* (2013.01); *A61B 5/6829* (2013.01); *A61B 8/00* (2013.01)

(58) Field of Classification Search
CPC ....... A61B 5/022; A61B 5/7275; A61B 5/046; A61B 5/6829; A61B 5/6824; A61B 5/6828; A61B 5/04525; A61B 5/6826; A61B 8/00; A61B 8/04
See application file for complete search history.

(56) References Cited

U.S. PATENT DOCUMENTS

| | | | | |
|---|---|---|---|---|
| 5,117,824 A | * | 6/1992 | Keimel ................ | A61N 1/3704 607/14 |
| 2002/0193695 A1 | * | 12/2002 | Koyrakh ............ | A61B 5/04525 600/510 |
| 2006/0258943 A1 | * | 11/2006 | Ogawa .................. | A61B 5/022 600/485 |
| 2008/0171396 A1 | * | 7/2008 | Fung ...................... | G01N 33/66 436/86 |
| 2011/0251505 A1 | * | 10/2011 | Narayan .............. | A61B 5/0422 600/515 |
| 2012/0259233 A1 | * | 10/2012 | Chan .................... | A61B 5/0002 600/484 |

(Continued)

OTHER PUBLICATIONS

Mašanauskienė, Edita, and Albinas Naudžiūnas. "Comparison of ankle-brachial index in patients with and without atrial fibrillation." Medicina (Kaunas) 47.12 (2011): 641-5.*

*Primary Examiner* — Navin Natnithithadha
*Assistant Examiner* — Andrey Shostak

(57) ABSTRACT

A hybrid model and diagnostic process for atrial fibrillation is provided. The present invention includes performing a combination of tests including an electrocardiogram signal analysis and a systolic pressure test. The results of the tests produce biomarkers for early detection of atrial fibrillation as well as for evaluating the severity of the disease.

8 Claims, 4 Drawing Sheets

(56) References Cited

U.S. PATENT DOCUMENTS

| | | | |
|---|---|---|---|
| 2014/0032122 A1* | 1/2014 | Bader | G06F 19/18 |
| | | | 702/19 |
| 2014/0058742 A1* | 2/2014 | Chari | G06F 19/345 |
| | | | 705/2 |
| 2014/0187519 A1* | 7/2014 | Cooke | G01N 33/6893 |
| | | | 514/165 |

* cited by examiner

HYBRID MODEL AND DIAGNOSTIC PROCESS FOR ATRIAL FIBRILLATION

CROSS-REFERENCE TO RELATED APPLICATION

This application claims the benefit of priority of U.S. provisional application No. 61/982,719, filed Apr. 22, 2014, the contents of which are herein incorporated by reference.

BACKGROUND OF THE INVENTION

The present invention relates to atrial fibrillation and, more particularly, to a hybrid model and diagnostic process for atrial fibrillation.

Atrial fibrillation (AFib) is a type of arrhythmia, where atria contract fast and/or irregularly due to a dysfunctional cardiac electrical system. AFib starts paroxysmally, and advances to a persistent/permanent stage. Early diagnosis and treatment in the paroxysmal stage, reduces chances of stroke. However, AFib usually remains undiagnosed until the disease progresses.

Current methods of diagnosing AFib are based on symptoms, such as palpitation and dizziness, after which an electrocardiogram (ECG) may be taken to check for AFib. However, the ECG pattern corresponding to AFib will occur only when the patient is experiencing an episode of AFib, which may not necessarily happen during the ECG recording, since AFib starts out initially as paroxysmal (rare occurrences). Thus AFib can remain undiagnosed till the disease progresses and episodes are more persistent, which by that time can increase the risk of stroke.

Long term ECG recording devices such as Holter or Event monitors are time consuming and do not give results in real time. The Echocardiography method is noninvasive, but requires special equipment. Also none of the techniques are for early diagnosis of the disease.

As can be seen, there is a need for an improved diagnostic process for atrial fibrillation.

SUMMARY OF THE INVENTION

In one aspect of the present invention, a method of diagnosing atrial fibrillation in a patient comprises: performing a systolic pressure test of a patient; performing an electrocardiogram of the patient to produce patient electrocardiogram data; and analyzing the patient electrocardiogram data and the systolic pressure test to make a determination of a diagnosis of atrial fibrillation.

In another aspect of the present invention, a method of diagnosing atrial fibrillation in a patient by performing a systolic pressure test comprising: determining a right and a left systolic brachial pressure and a right and a left ankle systolic pressure of the patient; determining a left side ankle brachial index and a right side ankle brachial index of the patient; analyzing the right and the left systolic brachial pressure, the right and the left ankle systolic pressure, and the ankle brachial index to make a determination of a diagnosis of atrial fibrillation.

These and other features, aspects and advantages of the present invention will become better understood with reference to the following drawings, description and claims.

DETAILED DESCRIPTION OF THE INVENTION

Figure 1:
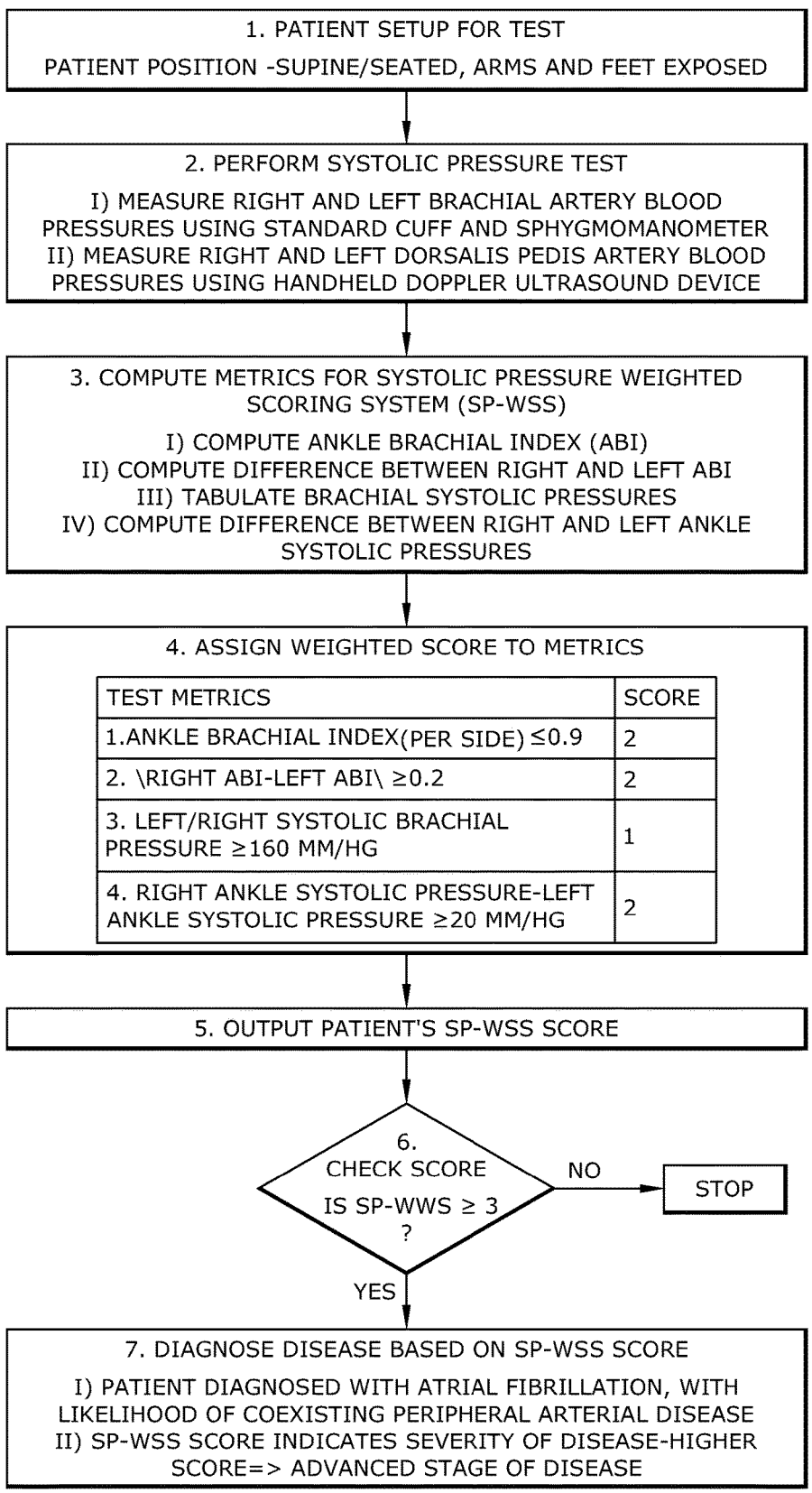
FIG. 1 is a flow chart of an embodiment of the present invention including a systolic pressure-weighted scoring system clinical procedure.

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

The present invention includes a combination of two non-invasive techniques, which are implemented by means of a multisensory hybrid device and diagnostic process. The present invention provides biomarkers for early detection of Atrial fibrillation as well as for evaluating the severity of the disease. By diagnosing Atrial fibrillation utilizing the present invention, treatment can immediately be started, which can reduce risk of stroke, save lives, and also improve the quality of life.

The present invention is based on gathering evidence of disease from multiple sources such as simple blood pressure test, and signal processing of standard ECG using a low cost ECG device. The present invention uses metrics with weighted scoring and minimum detection thresholds, Normal Sinus Rhythm ECG which can be performed right in the doctor's office, or by means of a home monitor kit, with no risk. Further, the present invention is non-invasive, and gives results in real time.

As mentioned above, the present invention combines a clinical blood pressure test and electrocardiogram signal analysis, along with patient medical history, to produce a hybrid model and diagnostic process that can be used as biomarkers for early detection of AFib as well as for evaluating the severity of the disease. The first test is a clinical procedure where the participants are subjected to the Systolic Pressure Test. The result of this test is used to generate a Weighted Scoring System (SP-WSS) that can be used to detect and assess the severity of AFib. The weighted scoring system creates a set of criteria based on brachial (arm) systolic pressures, ankle systolic pressures, and the difference in ankle to brachial systolic pressure ratios between right and left side of the body. Weights are assigned to each criterion, and a patient's total score is computed to form the Systolic Pressure Weighted Scoring System (SP-WSS). The score value indicates the presence and severity of the disease. Higher scores predict advanced stage of the disease and a greater risk for stroke. The second test is for early diagnosis, and involves a signal processing approach that creates an algorithm that can perform signal analysis on ECG of patients. The algorithm which is implemented in MATLAB (computer language for signal processing) produces a final averaged beat of the patient's ECG from which the physician can observe the width of the P wave, and the length of the PR interval, each of which are individual predictors of AFib. Finally, based on a patient's age and risk factors the hybrid technique combining both tests is used to create a diagnostic flowpath to be followed by physicians to detect and predict severity of AFib. Thus, the complete multisensory system acquires information from 3 sensors to provide a diagnosis of AFib.

Figure 2:
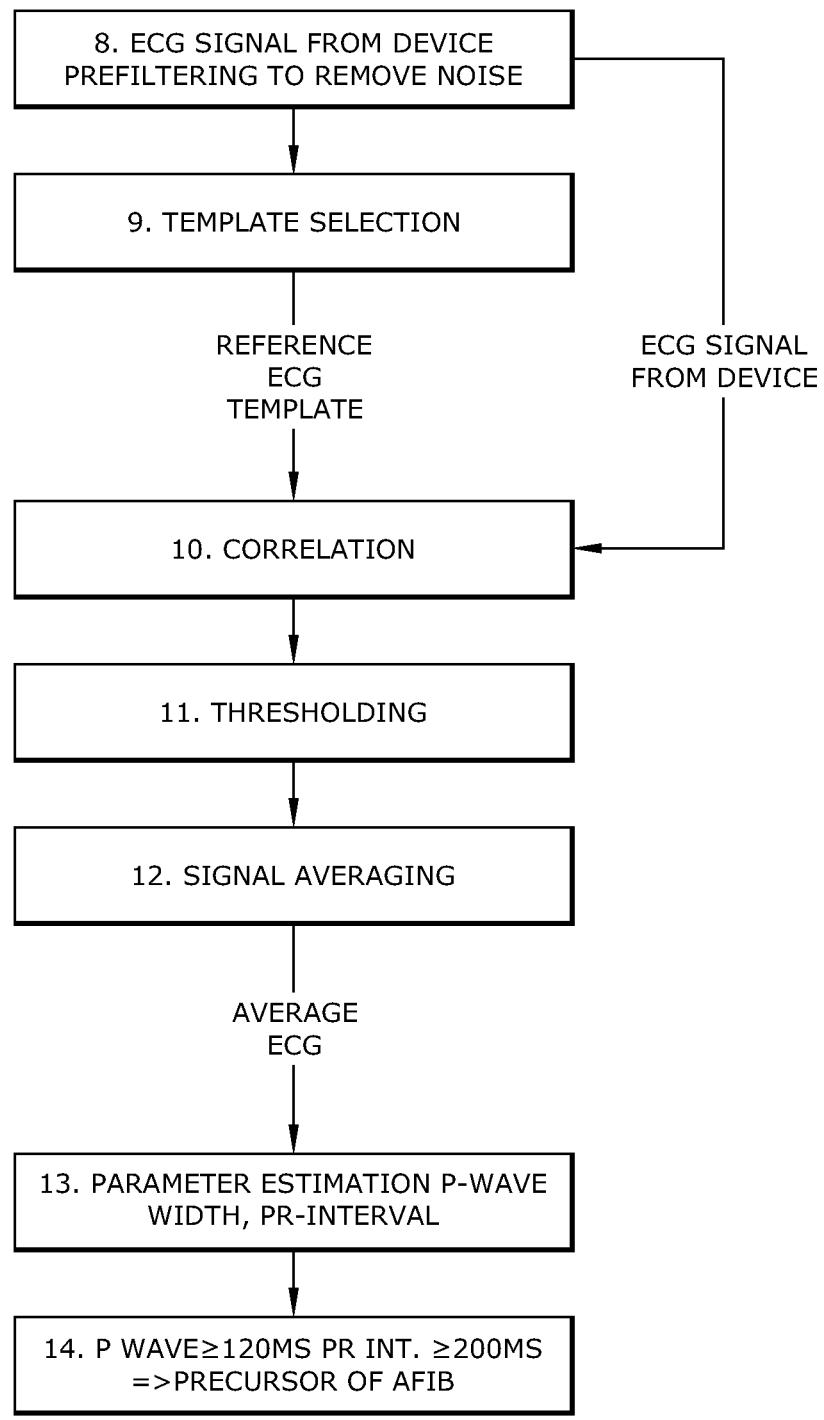
FIG. 2 is a flow chart of an embodiment of the present invention including an electrocardiogram signal analysis algorithm.
Figure 3:
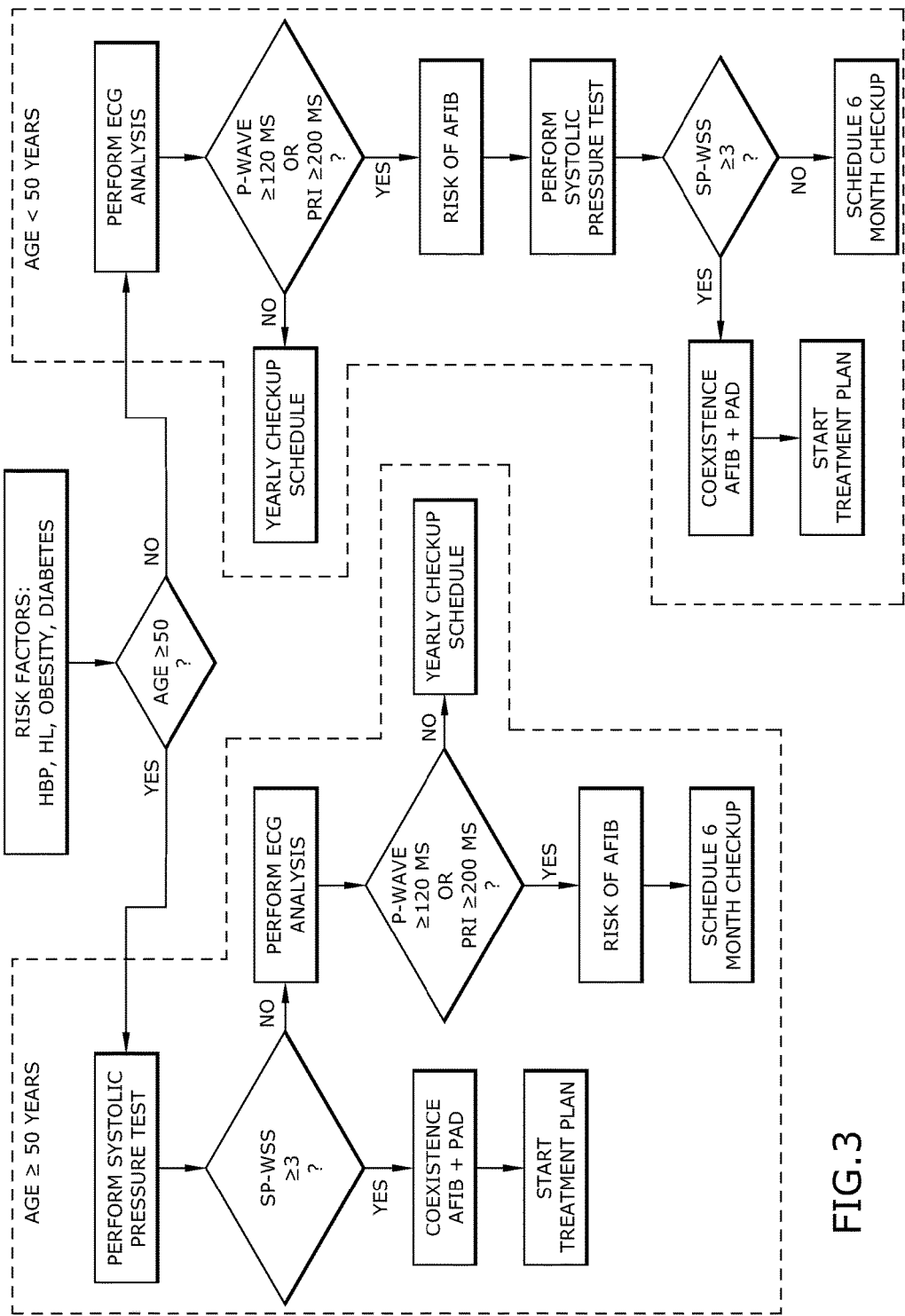
FIG. 3 is a flow chart outlining a diagnostic procedure combing the systolic pressure-weighted scoring system and the electrocardiogram signal analysis as a comprehensive tool to detect atrial fibrillation.

Referring to FIGS. 1 through 3, the present invention includes a combination of a clinical Systolic pressure test and an electrocardiogram signal analysis, to diagnose and determine the severity of AFib. FIG. 1 provides the method steps and the weighted system for performing the Systolic Pressure test. FIG. 2 provides the method steps for performing the electrocardiogram test. FIG. 3 provides the method steps for combining the Systolic Pressure test of FIG. 1 and the electrocardiogram test of FIG. 2 based on age and other risk factors.

The following steps are performed to compute the score for SP-WSS Test. To obtain patient's systolic pressures in arms and ankles, the patient can be in a seated or supine position. Measure the right and left brachial artery blood pressures using standard cuff and sphygmomanometer. Then measure the right and left dorsalis pedis artery blood pressures using a handheld doppler ultrasound device.

The weighted scoring system of the present invention may be based on four different metrics using blood pressure readings in the arms and feet. The metrics may include, but are not limited to, the ankle brachial index (ABI), the absolute value of the difference between the right and left ABI, the brachial systolic pressures, and the absolute value of the difference between the right and left dorsalis pedis (or posterior tibia) artery's systolic pressures. Weights are assigned to each of the metrics computed, based on the medical pathophysiological significance of the metric and statistical analyses.

For the ankle brachial index, each of the right and left side was assigned a score of two if the ABI is ≤0.9. Thus, ABIs 0.9 in the right and left sides include a total score of 4. The difference between the right and left ABI≥0.2 indicates an overall discrepancy in blood pressures in the peripheral arteries and is allotted a score of 2. High systolic blood pressures≥160 mm/Hg, in either left or right brachial artery is considered hypertensive, and assigned a score of 1. Finally, the right and left ankle systolic pressure differences of ≥20 mm/Hg is awarded a score of 2. The total SP-WSS score is calculated by adding the metric scores together. A score of ≥3 is classified as a diagnosis of AFib as well as an indication of a coexistence of Peripheral Artery Disease (PAD).

The ECG algorithm of the present invention processes and analyzes the ECG data, and produces conclusive diagnosis in real time, while the patient is in normal sinus rhythm when no fibrillation episodes are occurring. The stages of the algorithm are illustrated in the flow chart of FIG. 2.

First acquire about 10-15 minutes of a patient's normal sinus rhythm ECG data from the Limb Lead, which may be obtained using a low cost ECG device. A template resembling a clear patient ECG beat is selected from the initial beats, such as about 40-50 beats. This involves a user interactive method of examining sets of about 10 ECG beats at a time, to select a good representative beat. This selected beat is the reference ECG template. The reference ECG template is correlated with the entire ECG data taken from the patient. The reference template selects similar matches within the entire length of the ECG data. To retain valid matches and to reject stray artifacts, a variable threshold limits selection of only those beats that are matched to the reference template. The match may be within about 60%-85%, such as 70% matches. The valid ECG matches that pass the thresholding stage are summed along with the reference template and averaged, resulting in a single averaged ECG beat. Using the average ECG beat, the duration of the P wave and the duration of the PR interval is calculated. If either P wave duration is ≥120 ms or if the PR interval is ≥200 ms, the patient is diagnosed with inclination to AFib.

As mentioned above, FIG. 3 provides an outline of procedures that may be followed by physicians when combining the two non-invasive tests—Systolic Pressure test and ECG test. Based on risk factors such as hypertension, hyperlipidemia, obesity, diabetes, the patient is tested as follows. If the patient is less than 50 years of age, the ECG test is performed first. If P wave duration<120 ms, and PR interval<200 ms, Afib is not diagnosed, and patient can follow a yearly checkup schedule. If P wave duration≥120 ms, or if PR interval≥200 ms, the patient has a risk of AFib, and the SP-WSS test should be performed. If SP-WSS score<3, the patient is scheduled for a 6 month follow-up. Otherwise, if the SP-WSS score≥3, AFib is present with coexisting peripheral artery disease (PAD), and a treatment plan is immediately started.

For patients that are at least 50 years of age or older, the SP-WSS test may be performed first. If SP-WSS score≥3, AFib is present with coexisting peripheral artery disease, and treatment plan is immediately started. Otherwise, if SP-WSS score<3, patient is subjected to ECG test. If P wave duration<120 ms, and PR interval<200 ms, Afib diagnosed is not diagnosed, and the patient can follow a yearly checkup schedule. If the P wave duration≥120 ms, or if PR interval≥200 ms, the patient has risk of AFib, and should be scheduled for a 6 month follow up.

Figure 4:
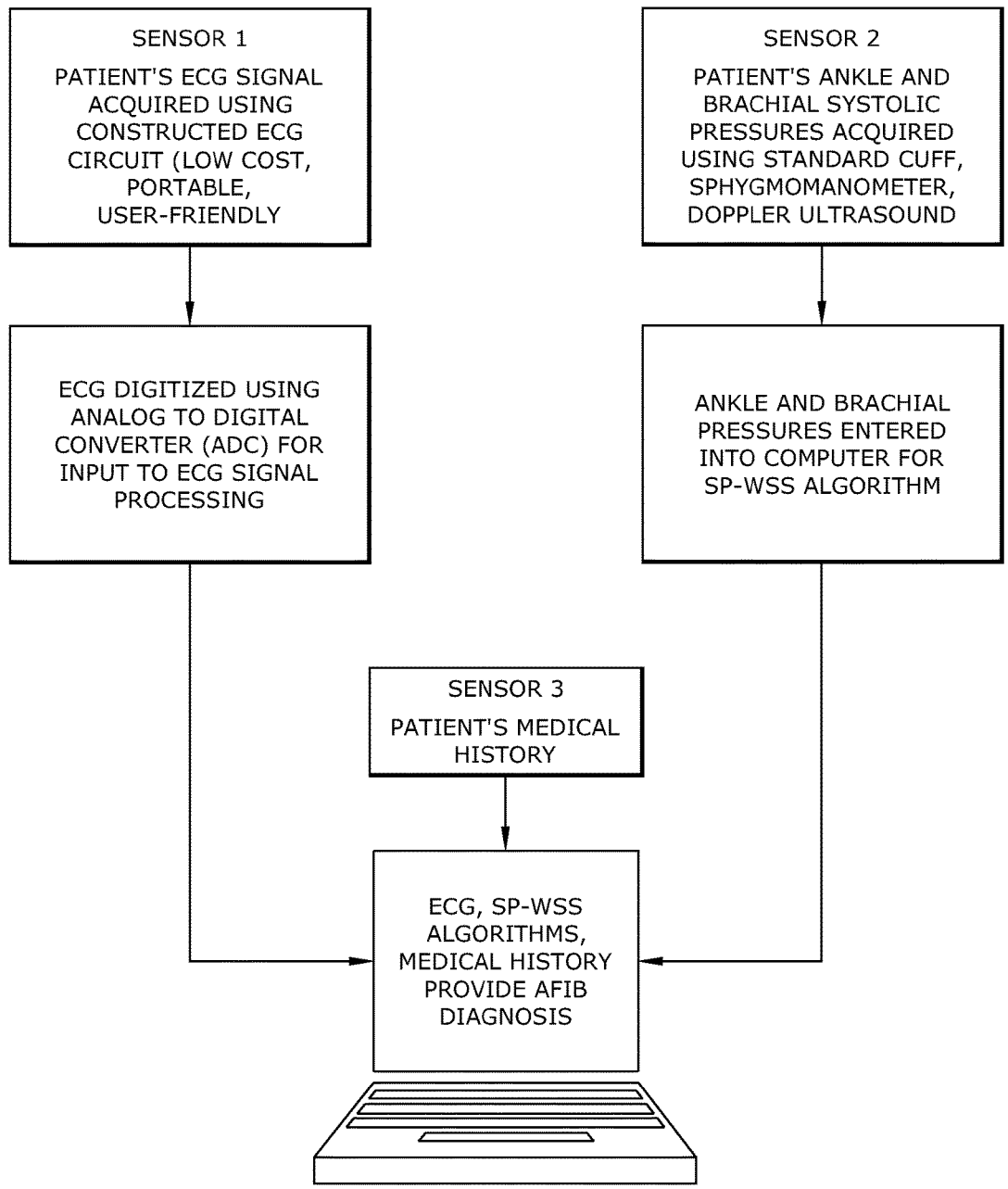
FIG. 4 is a flow chart of the overall block diagram depicting hybrid non-invasive multisensory test for diagnosing atrial fibrillation.

As illustrated in FIG. 4, the data may be recorded by a plurality of sensors and then entered to a computer to run the algorithms involved in the ECG and the SP-WSS test. Sensor 1, which may include any ECG machine, acquires the ECG signal using a constructed ECG circuit. An analog to digital converter (ADC) between the ECG machine and the computer enables digitization of the acquired ECG signal. Once the digitized ECG is uploaded to the computer, the ECG algorithm mentioned above may be implemented to determine the P wave duration and the PR interval. Sensor 2 may include a standard cuff, sphygmomanometer, Doppler ultrasound or other device to acquire blood pressure of the patient. The patient's ankle and brachial systolic pressures are acquired using Sensor 2. The data is entered into the computer and the computer performs the SP-WSS algorithm mentioned above. Sensor 3 may include patient medical history such as HBP, HL, obesity, diabetes as well as age. The data is combined using the computer and the Afib diagnosis is provided to the patient.

It should be understood, of course, that the foregoing relates to exemplary embodiments of the invention and that modifications may be made without departing from the spirit and scope of the invention as set forth in the following claims.

What is claimed is:
1. A non-invasive method of diagnosing atrial fibrillation in a patient, the method comprising:
  performing a systolic pressure test wherein systolic pressures of the patient are acquired from a plurality of arterial locations to compute metrics for a systolic pressure weighted score; wherein performing the systolic pressure test comprises:
    determining a right and a left brachial systolic pressure and a right and a left ankle systolic pressure;
  performing an electrocardiogram test wherein an electrocardiogram of the patient is acquired by processing an electrocardiogram signal to create an averaged electrocardiogram beat for electrocardiogram signal parameter estimation;
analyzing a combination of the systolic pressure weighted score of the systolic pressure test and the electrocardiogram signal parameters of the electrocardiogram test to make a determination of a diagnosis of atrial fibrillation in real time; wherein analyzing the systolic pressure weighted score of the systolic pressure test comprises:
  providing a plurality of the metrics, wherein the plurality of the metrics comprise an individual score for each metric, and a weight relative to one another, wherein a combination of the metrics enables the diagnosis of atrial fibrillation in real time; wherein the plurality of the metrics comprises:
    a) an ankle brachial index of a right side being less than or equal to 0.9;
    b) an ankle brachial index of a left side being less than or equal to 0.9;
    c) an absolute value of a difference of the ankle brachial index of the right side and the ankle brachial index of the left side being greater than or equal to 0.2;
    d) either the left or the right brachial systolic pressure being greater than or equal to 160 mm/Hg; and
    e) an absolute value of a difference of the right ankle systolic pressure and the left ankle systolic pressure being greater than or equal to 20 mm/Hg;
  deriving an optimal threshold score for the systolic pressure test; and
  comparing a total score for the systolic pressure test to the optimal threshold score;
performing the diagnosis while the patient is in normal sinus rhythm; wherein results of the diagnosis are made available to the patient in real time; wherein the determination of the diagnosis of atrial fibrillation in real time comprises determining the presence of two or more of the following: a) the ankle brachial index of the right side being less than or equal to 0.9; b) the ankle brachial index of the left side being less than or equal to 0.9; c) the absolute value of the difference of the ankle brachial index of the right side and the ankle brachial index of the left side being greater than or equal to 0.2; d) either the left or the right brachial systolic pressure being greater than or equal to 160 mm/Hg; and e) the absolute value of the difference of the right ankle systolic pressure and the left ankle systolic pressure being greater than or equal to 20 mm/Hg; and
starting a treatment plan in response to the diagnosis.

2. The method of claim 1, wherein performing the electrocardiogram test comprises:
acquiring patient electrocardiogram data for a 10-15 minute duration; and
processing the patient electrocardiogram data with a computing device through signal processing steps of:
  retrieving a template comprising a beat from the electrocardiogram data, the retrieving being based on a user selection;
  correlating the template with the duration of the acquired electrocardiogram data to retrieve a plurality of matched beats; wherein the plurality of matched beats have a measure of similarity to the template above a threshold amount; and
  averaging an amplitude of the plurality of matched beats to form an averaged beat for determining the electrocardiogram signal parameters; wherein the electrocardiogram signal parameters, including a P wave width and a PR interval duration, are determined from the averaged beat; and wherein the determination of the P wave width and the PR interval duration of the averaged beat enables the diagnosis of atrial fibrillation in real time while the patient is in normal sinus rhythm.

3. The method of claim 2, wherein analyzing the electrocardiogram signal parameters comprises:
extracting parameters including the width of the P wave and the duration of the PR interval from the averaged beat in response to the user selection;
wherein the parameters of P wave width and PR interval duration comprise an equal weight in the detection of atrial fibrillation; wherein if the P wave width is greater than or equal to 120 ms, or if the PR interval duration is greater than or equal to 200 ms, the patient is diagnosed with atrial fibrillation.

4. The method of claim 2, wherein the threshold amount for retrieving the plurality of matched beats that match the template is an adaptive threshold amount that is variable between 60% to 85%.

5. The method of claim 1, wherein metrics (a) through (c) and (e) comprise an equal weight, and wherein metric (d) comprises a lesser weight than metrics (a) through (c) and (e).

6. The method of claim 1, wherein the total score is indicative of severity of atrial fibrillation and its coexistence with peripheral arterial disease; and wherein the total score enables determining the treatment plan to be started in response to the diagnosis.

7. A method of diagnosing atrial fibrillation in a patient, the method comprising:
performing a systolic pressure test comprising:
  determining a right and a left brachial systolic pressure and a right and a left ankle systolic pressure of the patient; and
  determining a left side ankle brachial index and a right side ankle brachial index of the patient;
deriving a plurality of metrics based on the systolic pressures; wherein the plurality of metrics comprise an individual score for each metric, a weight relative to one another, and a threshold score for the systolic pressure test;
calculating a total score of the systolic pressure test to enable making a determination of a diagnosis of atrial fibrillation in real time; wherein the diagnosis is performed while the patient is in normal sinus rhythm;
performing an electrocardiogram test of the patient to obtain patient electrocardiogram data for electrocardiogram signal parameter estimation, wherein performing the electrocardiogram test comprises;
  retrieving a template comprising a beat from the electrocardiogram data;
  correlating the template with the duration of the obtained electrocardiogram data to retrieve a plurality of matched beats; wherein the plurality of matched beats have a measure of similarity to the template above a threshold amount; and
  averaging an amplitude of the plurality of matched beats to form an averaged beat for determining the electrocardiogram signal parameters;
estimating the electrocardiogram signal parameters, the parameters comprising a P wave width and a PR interval duration of the averaged beat, wherein the parameters of P wave width and PR interval duration comprise an equal weight in the diagnosis of atrial fibrillation, wherein the determination of the diagnosis of atrial fibrillation in real time comprises determining one or more of the following: (1) the P wave width being greater than or equal to 120 ms, and (2) the PR interval duration being greater than or equal to 200 ms;

analyzing the estimated electrocardiogram signal parameters, the right and the left brachial systolic pressure, the right and the left ankle systolic pressure, and the right side and the left side ankle brachial index to diagnose atrial fibrillation; and starting a treatment plan based on the diagnosis.

8. The method of claim 7, wherein the total score indicates a presence and severity of peripheral arterial disease.

\* \* \* \* \*